(12) United States Patent
Nomoto et al.

(10) Patent No.: US 7,727,213 B2
(45) Date of Patent: Jun. 1, 2010

(54) ABSORBENT ARTICLE

(75) Inventors: Takashi Nomoto, Kagawa-ken (JP); Chinatsu Nanbu, Kagawa-ken (JP)

(73) Assignee: Unicharm Corporation, Ehime (JP)

( * ) Notice: Subject to any disclaimer, the term of this patent is extended or adjusted under 35 U.S.C. 154(b) by 847 days.

(21) Appl. No.: 11/540,029

(22) Filed: Sep. 29, 2006

(65) Prior Publication Data

US 2007/0100307 A1    May 3, 2007

(30) Foreign Application Priority Data

Nov. 2, 2005   (JP) ............................. 2005-320049

(51) Int. Cl.
*A61F 13/15* (2006.01)
(52) U.S. Cl. ................. 604/385.201; 604/385.101; 604/378; 604/380
(58) Field of Classification Search .......... 604/385.101, 604/378, 380
See application file for complete search history.

(56) References Cited

U.S. PATENT DOCUMENTS

| | | | |
|---|---|---|---|
| 1,376 A | 10/1839 | Rose | |
| 4,605,404 A | 8/1986 | Sneider | |
| 4,758,241 A | 7/1988 | Papajohn | |
| 5,221,275 A | 6/1993 | Van Iten | |
| H1376 H | 11/1994 | Osborn, III et al. | |
| 6,491,674 B1 | 12/2002 | Salerno | |
| 2006/0129114 A1* | 6/2006 | Mason et al. | 604/361 |

FOREIGN PATENT DOCUMENTS

| | | |
|---|---|---|
| EP | 0 130 848 | 1/1985 |
| JP | H07-024007 A | 1/1995 |
| JP | H08-511706 A | 12/1996 |
| JP | H09-117471 A | 5/1997 |
| JP | 11-076304 | 3/1999 |
| JP | 2000-152957 A | 6/2000 |
| JP | 2000-342626 A | 12/2000 |

(Continued)

OTHER PUBLICATIONS

Singapore Office Action mailed Apr. 20, 2009 in Singapore Patent Application No. 200802606-4.

(Continued)

*Primary Examiner*—Jacqueline F. Stephens
(74) *Attorney, Agent, or Firm*—Brinks Hofer Gilson & Lione

(57) ABSTRACT

An absorbent article that prevents a discharged matter from leaking out, and also prevents a wearer's sensation of wearing a sanitary napkin from worsening is provided. The absorbent article of the present invention includes a liquid-permeable surface sheet, a liquid-permeable back sheet, an absorbent body disposed between the surface sheet and the back sheet, and an intermediate portion disposed between the surface sheet and the absorbent body. The absorbent part 4 includes an absorbent body center portion and an absorbent body posterior portion continuously formed on a posterior side in the longitudinal direction D of the absorbent body center portion. The intermediate portion includes a first intermediate sheet disposed between the surface sheet and the absorbent body center portion and a second intermediate sheet disposed between the surface sheet and at least the absorbent body posterior portion. The liquid-transport property of the second intermediate sheet is different from that of the first intermediate sheet.

15 Claims, 6 Drawing Sheets

FOREIGN PATENT DOCUMENTS

| | | |
|---|---|---|
| JP | D1154999 | 10/2002 |
| JP | 2003-24371 A | 1/2003 |
| JP | D1169280 | 3/2003 |
| JP | D1169425 | 3/2003 |
| JP | 2003-093438 | 4/2003 |
| JP | D1174600 | 6/2003 |
| JP | D1174983 | 6/2003 |
| JP | D1175692 | 6/2003 |
| JP | D1176343 | 6/2003 |
| JP | D1176373 | 6/2003 |
| JP | D1176374 | 6/2003 |
| JP | D1196974 | 2/2004 |
| JP | D1196975 | 2/2004 |
| JP | D1197310 | 2/2004 |
| JP | D1198639 | 3/2004 |
| JP | 2004-216172 | 8/2004 |
| JP | 2004-229766 A | 8/2004 |
| JP | 2004-298411 A | 10/2004 |
| JP | 2005-237793 A | 9/2005 |
| JP | 2005-287843 | 10/2005 |
| TW | 581621 | 3/2004 |
| TW | 581624 | 3/2004 |
| TW | 582957 | 4/2004 |
| WO | WO 95/00093 | 1/1995 |
| WO | WO 2005/115296 | 12/2005 |

OTHER PUBLICATIONS

Official Action issued to Egyptian Application No. PCT 699/2008, mailed Aug. 2, 2009 (no translation.

\* cited by examiner

ABSORBENT ARTICLE

This application is based on and claims the benefit of priority from Japanese Patent Application No. 2005-320049, filed on Nov. 2, 2005, the content of which is incorporated herein by reference.

BACKGROUND OF THE INVENTION

1. Field of the Invention

The present invention relates to an absorbent article.

2. Related Art

Conventionally, as a sanitary napkin suitable for being worn by a woman during menstruation while sleeping or the like, for example, a sanitary napkin which is extended backward to cover the coccyx has been used. However, when the conventional sanitary napkin is used for a long time in a lying posture, while sleeping or the like, the sensation of being worn may worsen, and the leakage of a discharged matter may be caused. In such a sanitary napkin, for preventing the sensation of wearing a sanitary napkin from worsening, the leakage of discharged matter, and the like, in addition to an improvement in a surface sheet, brought into contact with the body and an absorbent body for absorbing the discharged matter, an improvement in a second sheet part to be positioned between the surface sheet and the absorbent body has been achieved.

For instance, as shown in FIG. 7 which is one of the sanitary napkins disclosed in Japanese Unexamined Publication No. Hei 08-511706, an invention is proposed in which a certain absorbent strip 910 is combined with a fluid directing strip 920 to direct a discharged matter to move toward the exterior edge portion of an absorbent article, thereby preventing the sensation of wearing a sanitary napkin from worsening at the excretion part of the body.

The sanitary napkin disclosed in Japanese Unexamined Publication No. Hei 08-511706 can direct the discharged matter to move toward the exterior edge portion of an absorbent article by combining a certain absorbent strip 910 with a fluid directing strip 920. Therefore, a worsening of the sensation of wearing a sanitary napkin at the excretion part of the body can be prevented. However, as shown in Japanese Unexamined Publication No. Hei 08-511706, when the discharged matter is directed to move toward the exterior edge portion of the absorbent article, the leakage of discharged matter from the posterior of the absorbent article can be promoted. This is because the vaginal opening portion directs in a direction perpendicular to the floor when the wearer lies on her back and thus the blood tends to flow to the floor. Therefore, the present invention intends to prevent the leakage of a discharged matter, and also a worsening of the sensation of wearing a sanitary napkin, which have not been solved in Japanese Unexamined Publication No. Hei 08-511706.

SUMMARY OF THE INVENTION

The present invention has been worked out in view of the shortcomings in the prior art set forth above. It is therefore an object of the present invention to provide an absorbent article that prevents a discharged matter from leaking out, and also prevents the wearer's sensation of wearing a sanitary napkin from becoming worse.

For attaining the above object, the present invention disposes an intermediate portion having different liquid-transport properties at the respective locations thereof to be brought into contact with the wearer's body depending on the mode of usage. The present inventors have found out that the leakage of a discharged matter after prolonged use in a lying posture, and an increase in the feeling of discomfort from wearing a sanitary napkin can be prevented. Therefore, the present inventors have invented an absorbent article as described below.

(1) An absorbent article including: a liquid-permeable surface sheet; a liquid-impermeable back sheet; an absorbent body having an absorbent portion and an absorbent body posterior portion continuously formed on the posterior side in the longitudinal direction of the absorbent body center portion; and an intermediate portion that includes a first intermediate sheet and a second intermediate sheet, in which the first intermediate sheet is disposed between the surface sheet and the absorbent body and disposed between the surface sheet and the absorbent body center portion, while the second intermediate sheet is disposed between the surface sheet and at least the absorbent body posterior portion, and the liquid-transport property of the second intermediate sheet is different from the liquid-transport property of the first intermediate sheet.

According to a first aspect of the present invention, the absorbent article includes an absorbent part having an absorbent body center portion, and an absorbent body posterior portion, in which the absorbent body posterior portion is continuously formed in the longitudinal direction LD of the absorbent body center portion. An intermediate portion includes a first intermediate sheet and a second intermediate sheet, in which the first intermediate sheet is disposed between the surface sheet and the absorbent body center portion, and the second intermediate sheet is disposed between the surface sheet and at least the absorbent body posterior portion. The liquid-transport property of the second intermediate sheet is different from the liquid-transport property of the first intermediate sheet.

In this context, the central absorbent portion containing the absorbent body center portion is an area that mainly absorbs a discharged matter from the excretion part of the wearer's body. For instance, the predetermined area of the central absorbent portion is brought into contact with the excretion part of the body to absorb the discharged matter by the absorbent body center portion. On the surface sheet of the central absorbent portion, the first intermediate sheet is disposed. The first intermediate sheet is a sheet having a liquid-transport property, which is different from that of the second intermediate sheet. In other words, for example, they have different liquid permeabilities and liquid-drawing abilities with respect to each other.

The posterior absorbent portion containing he absorbent body posterior portion is an area that absorbs the discharged matter which could not be absorbed by the central absorbent portion, the discharged matter running along the wearer's body from the excretion part of the body, or the like. On the surface sheet of the posterior absorbent portion, the second intermediate sheet is disposed. The second intermediate sheet is a sheet having its own liquid-transport property, which is different from that of the first intermediate sheet. As described above, for example, they have different liquid permeabilities and liquid-drawing abilities with respect to each other.

The first intermediate sheet is disposed between the surface sheet and the absorbent body center portion. For instance, when the absorbent article is used in a lying posture, the central absorbent portion is substantially perpendicular to the surface of a floor. Thus, the discharged matter may tend to flow to the posterior absorbent portion on the side of the floor's surface. Therefore, the first intermediate sheet is desired to quickly transport the discharged matter to the absorbent body center portion, so that, for example, a sheet part having high liquid permeability can be employed.

The second intermediate sheet is disposed between the surface sheet and the absorbent body posterior portion. For instance, in the case of using the absorbent article in a lying posture, a small amount of the discharged matter may flow to the posterior absorbent portion when the discharged matter could not be sufficiently absorbed by the central absorbent portion or run along the wearer's body from the excretion part of the body. Therefore, the first intermediate sheet is desired to quickly absorb a small amount of the flowing discharged matter, so that, for example, a sheet part having high-drawing ability can be employed.

Here, the first and second intermediate sheets may be made of different materials, respectively. Alternatively, the first and second intermediate sheets may be constructed such that they are formed using the same material and then subjected to different processes to adjust their liquid permeabilities.

In a second aspect of the absorbent article as described in the first aspect of the present invention, the liquid-transport property is liquid permeability, and the first intermediate sheet has a higher liquid permeability than the second intermediate sheet.

According to the second aspect of the present invention, the absorbent article is constructed such that the liquid permeability of the first intermediate sheet is higher than that of the second intermediate sheet. In particular, a sheet part having a short permeation period for a given liquid, which is measured by a strike-through method, can be used. For instance, the first sheet has a permeation period of 3% or more, preferably 5% or shorter than that of the second intermediate sheet. Therefore, for example, the central absorbent portion, on which the first intermediate sheet is disposed, can quickly transport the discharged matter from the excretion part of the wearer's body to the absorbent body center portion. Consequently, it is possible to prevent the discharged matter from leaking out and also prevent the wearer's sensation of wearing a sanitary napkin from becoming worse.

In a third aspect of the absorbent article as described in the second aspect of the present invention, the first intermediate sheet is further provided with a plurality of liquid-passage pores.

According to the third aspect of the present invention, the absorbent article is constructed such that the first intermediate sheet is further provided with a plurality of liquid-permeable pores. The liquid-permeable pores can be formed by a predetermined process for forming pores. For instance, the predetermined process for forming pores is carried out while the surface sheet and the first intermediate sheet are being disposed in laminate, thereby also providing the surface sheet with pores communicating with the first intermediate sheet. A plurality of the liquid-permeable pores is provided, so that the discharged matter from the excretion part of the wearer's body can be quickly transported to the absorbent body center portion, thereby allowing a further increase in liquid permeability.

In a fourth aspect of the absorbent article as described in the first aspect of the present invention, the liquid-transporting properties is liquid-drawing ability, and the second intermediate sheet has a higher liquid-drawing property than the first intermediate sheet.

According to the fourth aspect of the present invention, the second intermediate sheet is constructed such that its liquid-drawing ability is higher than that of the first intermediate sheet. Therefore, the absorbent article is able to quickly draw, for example a small amount of the discharged matter that could not be absorbed by the central absorbent portion or a small amount of the discharged matter flowing out of the central absorbent portion, into the side of the absorbent body posterior portion. Consequently, the absorbent article is able to prevent the discharged matter from leaking out of the posterior side and also prevent the wearer's sensation of wearing the sanitary napkin from becoming worse.

In a fifth aspect of the absorbent article as described in a fourth aspect of the present invention, the second intermediate sheet has a stronger capillary action than the first intermediate sheet.

According to the fifth aspect of the present invention, the absorbent article is constructed such that the capillary action of the second intermediate sheet is stronger than that of the first intermediate sheet. Therefore, the absorbent article is able to quickly draw, for example a small amount of the discharged matter that could not be absorbed by the central absorbent portion or a small amount of the discharged matter flowing out of the central absorbent portion, into the side of the absorbent body posterior portion. Consequently, the absorbent article is able to prevent the discharged matter from leaking out of the posterior side and also prevent the wearer's sensation of wearing the sanitary napkin from becoming worse.

In a sixth aspect of the absorbent article as described in the fourth aspect of the present invention, the second intermediate sheet has a higher hydrophilic property than the first intermediate sheet.

According to the sixth aspect of the present invention, the absorbent article is constructed such that the hydrophilic property of the second intermediate sheet is stronger than that of the first intermediate sheet. Therefore, the absorbent article is able to quickly draw, for example a small amount of the discharged matter that could not be absorbed by the central absorbent portion or a small amount of the discharged matter flowing out of the central absorbent portion, into the side of the absorbent body posterior portion. Consequently, the absorbent article is able to prevent the discharged matter from leaking out of the posterior side and also prevent the wearer's sensation of wearing the sanitary napkin from becoming worse.

In a seventh aspect of the absorbent article as described in any of aspects one through six of the present invention, the second intermediate sheet is continuously disposed in parallel with the first intermediate sheet in the longitudinal direction.

According to the seventh aspect of the present invention, in the absorbent article, the second intermediate sheet is continuously disposed in parallel with the first intermediate sheet in the longitudinal direction LD. Therefore, the second intermediate sheet can absorb a small amount of the discharged matter flowing out of the side of the central absorbent portion in midstream, so that, for example, it can prevent the discharged matter from leaking out of the posterior side.

In an eighth aspect of the absorbent article as described in any of aspects one through six of the present invention, a part of the second intermediate sheet is disposed in laminate, being overlapped in the direction of width by at least a part of the first intermediate sheet.

According to the eighth aspect of the present invention, the absorbent article is constructed in that a part of the second intermediate sheet is disposed in laminate, being overlapped in the direction of width WD by at least a part of the first intermediate sheet. Consequently, as described above, a small amount of the discharged matter flowing out of the side of the central absorbent portion can be absorbed in midstream. Thus, for example, it can prevent the discharged matter from leaking out of the posterior side of the absorbent article. In addition, in the production process of the absorbent article, the laminate arrangement of the first and second intermediate sheets is favorable for the manufacturer because there is no need for accurate positioning of both the first and second intermediate sheets.

In a ninth aspect of the absorbent article as described in any of aspects one through eight of the present invention, further comprising a folding part predetermined to be folded substantially perpendicular to the longitudinal direction LD, where the first intermediate sheet is only disposed on one side of the folding part in the longitudinal direction LD, while part of a second intermediate sheet is disposed on the other side of the folding part in the longitudinal direction LD.

According to the ninth aspect of the present invention, the absorbent article is further provided with a folding part predetermined to be folded substantially perpendicular to the longitudinal direction LD. In addition, the first intermediate sheet is only disposed on one side of the folding part in the longitudinal direction LD, while part of a second intermediate sheet is disposed on the other side of the folding part in the longitudinal direction LD. For instance, when the first intermediate sheet is used in a lying posture, it is disposed in the front side of the folding part, which is in a state of being raised substantially perpendicular to the surface of a floor. In other words, the first intermediate sheet is disposed on the central absorbent portion which is brought into contact with the excretion part of the wearer's body, thereby allowing the discharged matter to quickly permeate to the absorbent body center portion. A part of the second intermediate sheet is disposed on the posterior side of the absorbent article, which becomes substantially parallel to the floor's surface when the wearer takes in a lying posture. In other words, the second intermediate sheet quickly absorbs a small amount of the discharged matter that could not be absorbed by the central absorbent portion or flowing along the wearer's body or the like from the excretion part of the body.

In a tenth aspect of the absorbent article as described in any of aspects one through nine of the present invention, the second intermediate sheet is thicker than the first intermediate sheet, and the second intermediate sheet is longer than the first intermediate sheet in the longitudinal direction.

According to the tenth aspect of the present invention, the absorbent article can be constructed such that the second intermediate sheet is thicker than the first intermediate sheet, and the second intermediate sheet is longer than the first intermediate sheet in the longitudinal direction LD. Such a configuration of the absorbent article contributes to an increase in liquid-drawing ability of the second intermediate sheet while retaining the high liquid permeability of the first intermediate sheet.

According to the present invention, an absorbent article, which prevents a discharged matter from leaking out and also prevents the wearer's sensation of wearing the sanitary napkin from becoming worse, can be provided.

DETAILED DESCRIPTION OF THE INVENTION

Figure 1:
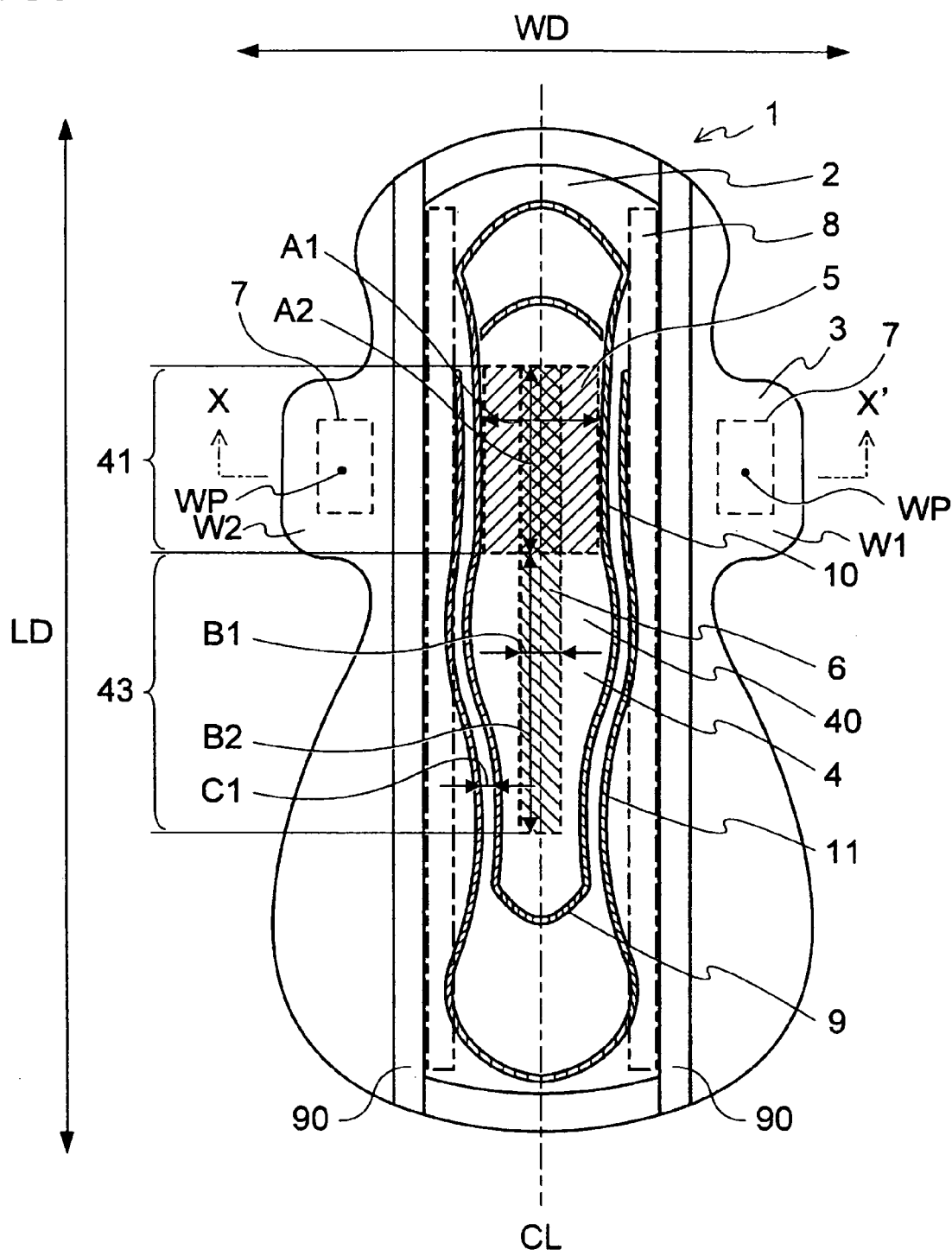
FIG. 1 is a plain view showing an absorbent article according to a first embodiment of the present invention.
Figure 2:
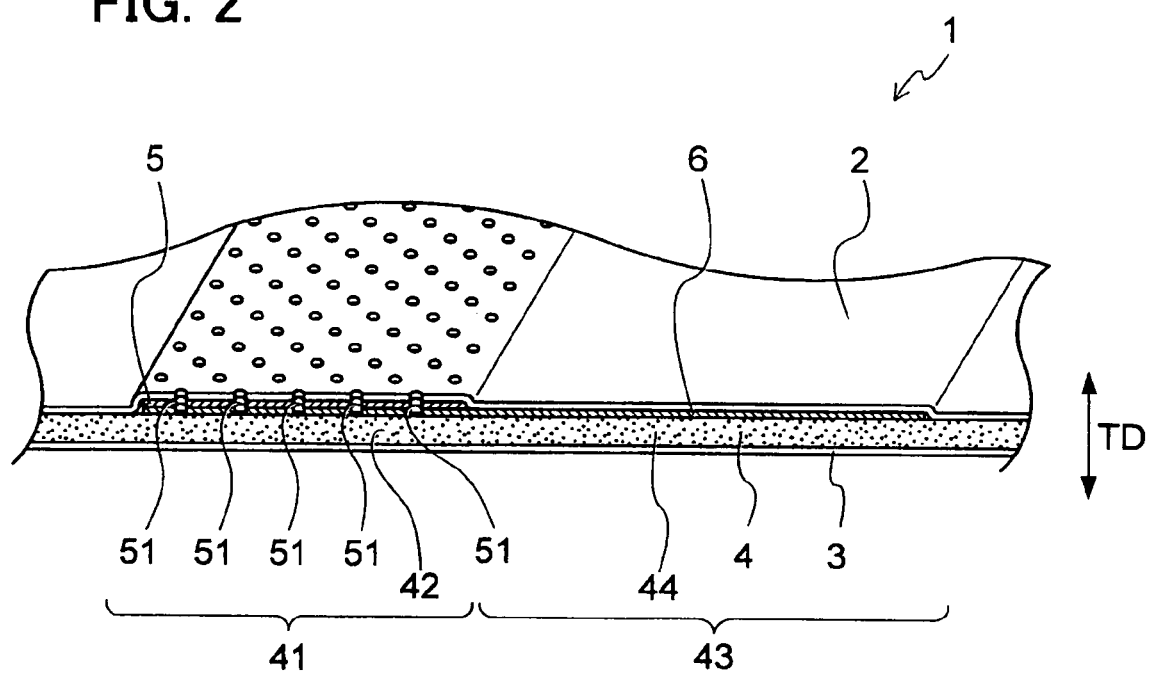
FIG. 2 is a cross-sectional view taken along the centerline of the absorbent article according to the first embodiment of the present invention.
Figure 3:
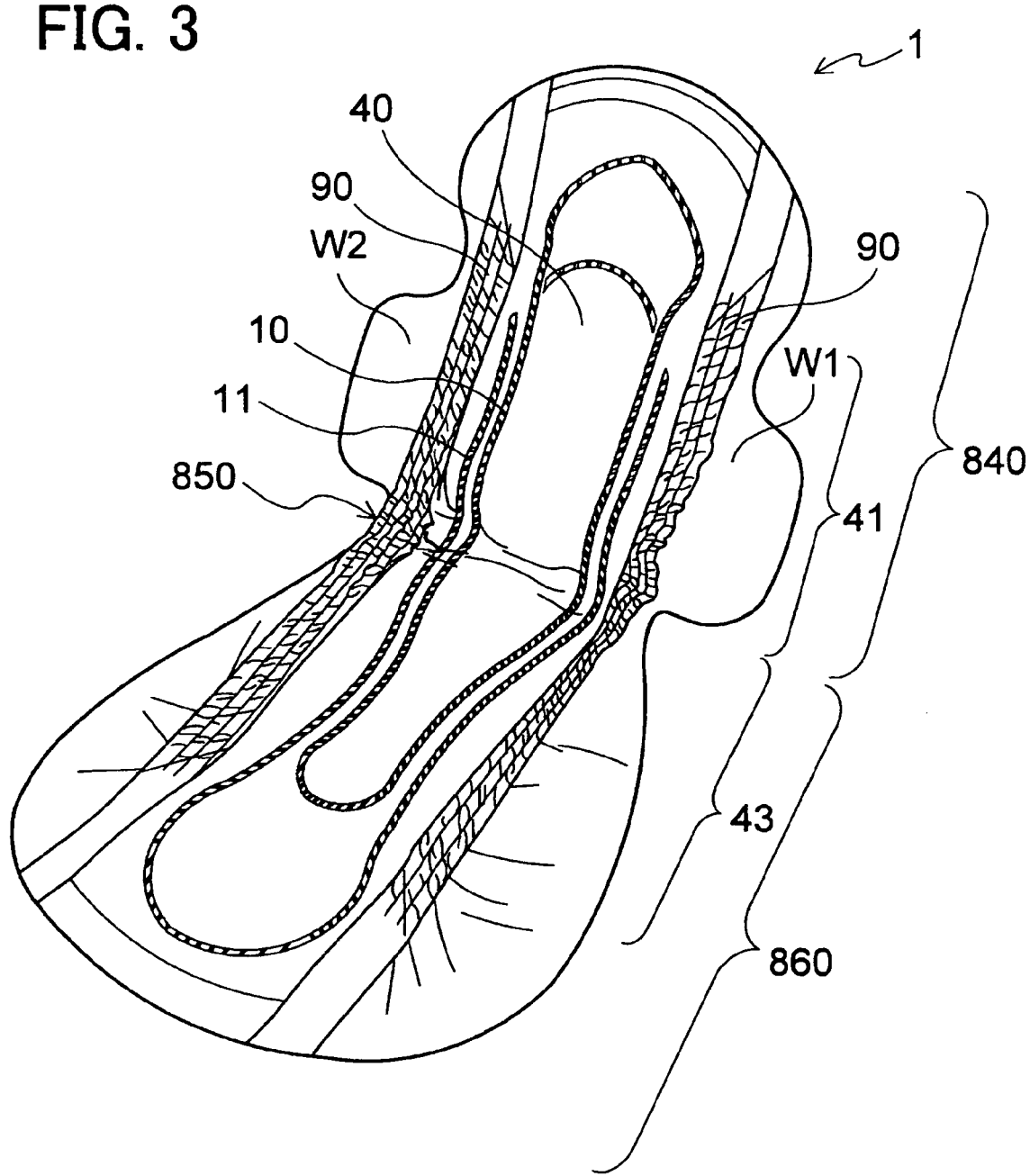
FIG. 3 is a perspective view showing the absorbent article according to the first embodiment of the present invention.
Figure 4:
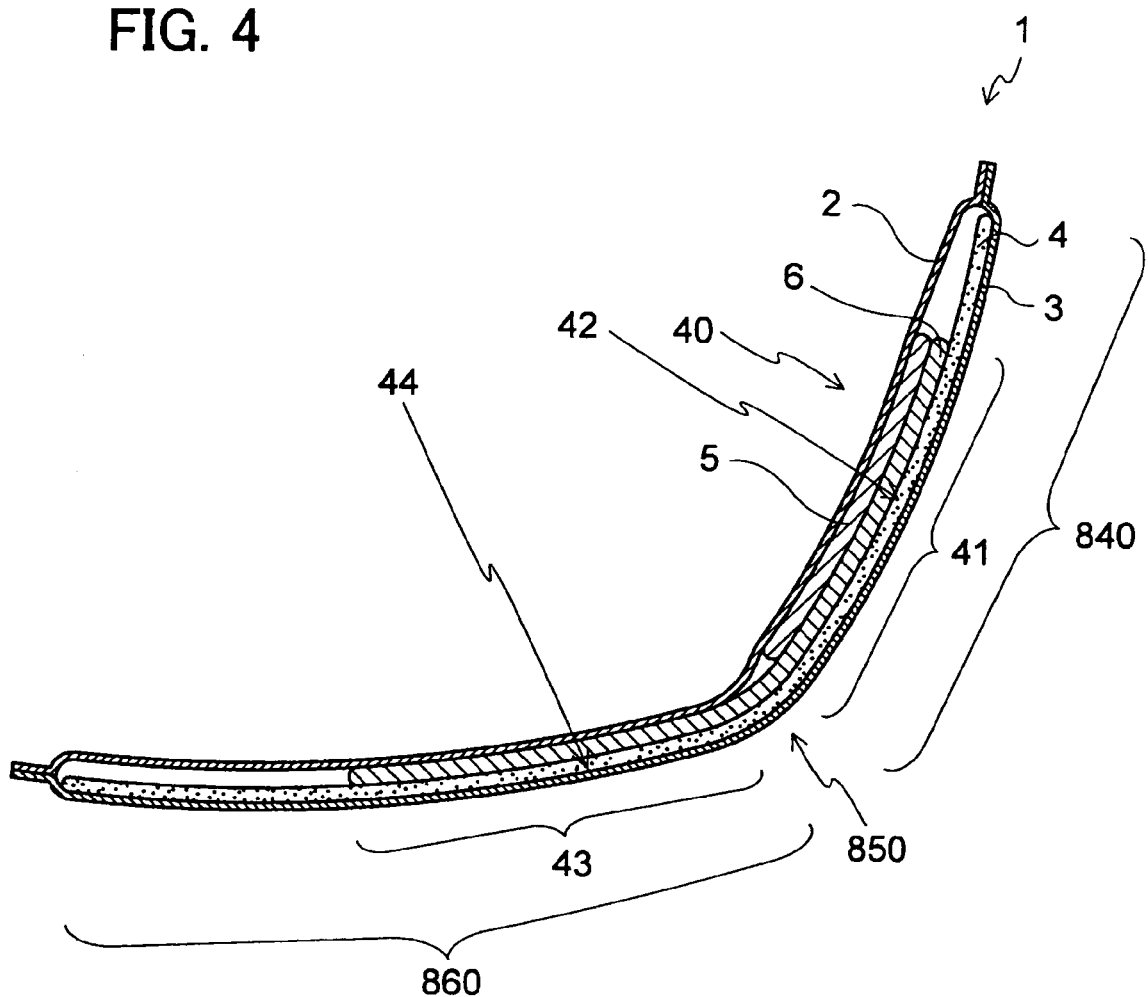
FIG. 4 is a cross-sectional view taken along a centerline of the absorbent article shown in FIG. 3.
Figure 5:
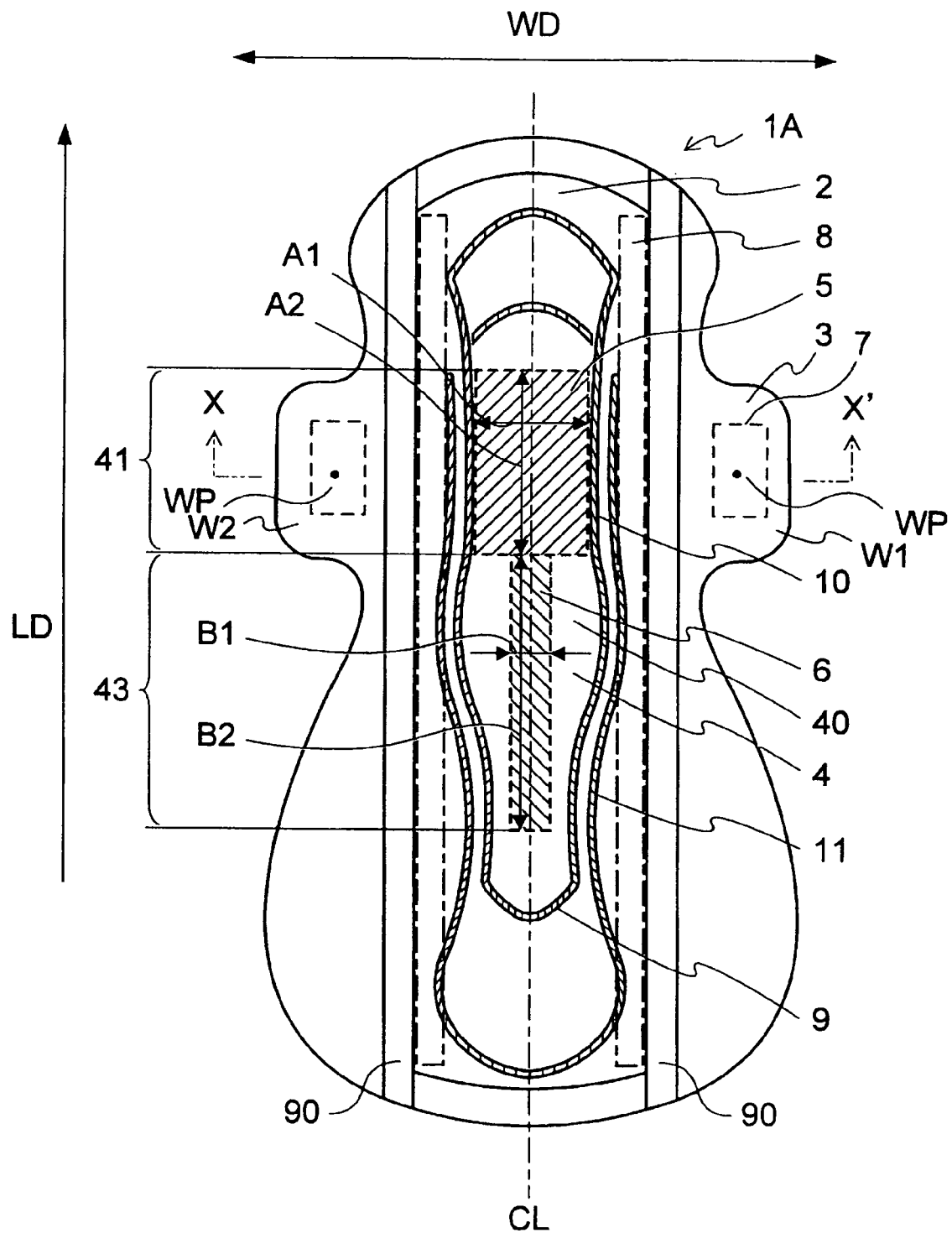
FIG. 5 is a plain view showing an absorbent article according to a second embodiment of the present invention.
Figure 6:
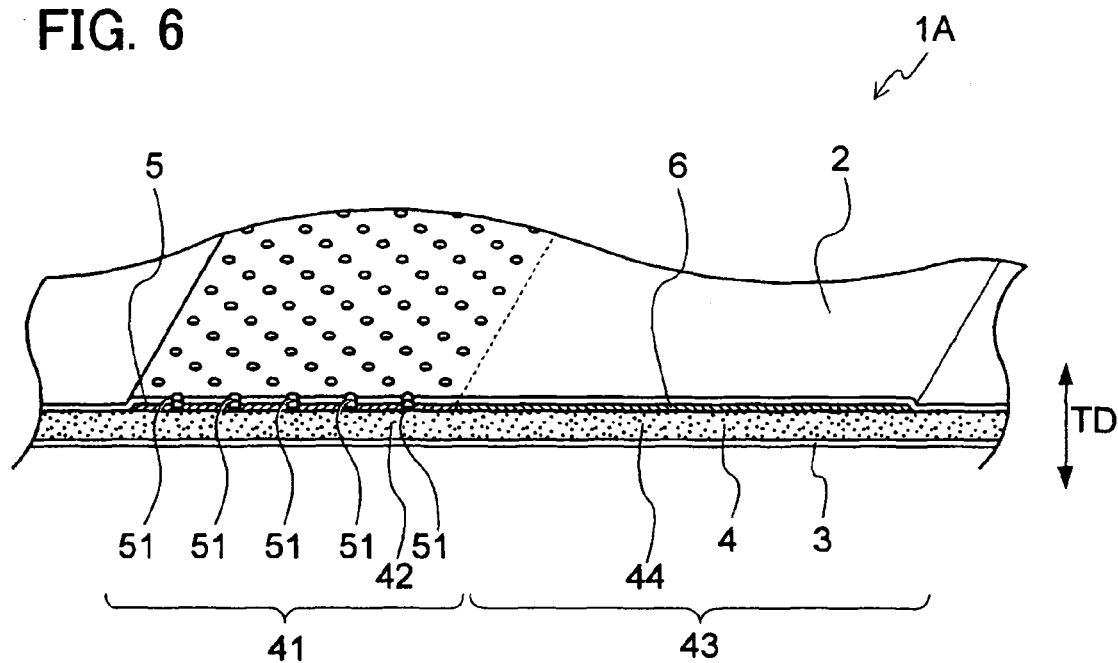
FIG. 6 is a cross-sectional view taken along the centerline of the absorbent article according to the second embodiment of the present invention.
Figure 7:
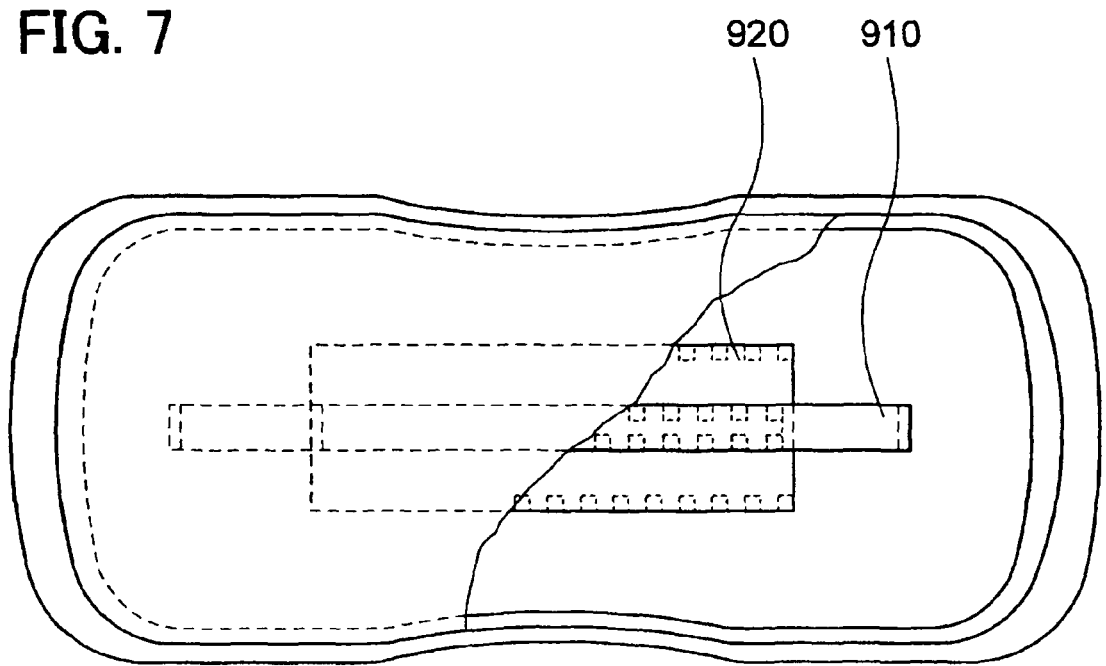
FIG. 7 is a plain view showing the conventional absorbent article.

FIG. 1 is a plain view showing an absorbent article according to a first embodiment of the present invention. FIG. 2 is a cross-sectional view taken along a centerline of the absorbent article according the first embodiment of the present invention. FIG. 3 is a perspective view of the absorbent article in use according to the first embodiment of the present invention. FIG. 4 is a cross-sectional view taken along a centerline of the absorbent article in FIG. 3. FIG. 5 is a plan view showing an absorbent article according to a second embodiment of the present invention. FIG. 6 is a cross-sectional view taken along a centerline of the absorbent article according to the second embodiment of the present invention. FIG. 7 is a plain view showing an absorbent article according to the conventional technology.

[1] Overall Configuration of Absorbent Article

The overall configuration of the absorbent article of the present invention will be described with reference to an absorbent article 1 according to a first embodiment of the present invention.

[1.1] General View

As shown in FIGS. 1 and 2, the absorbent article 1 of the present invention is a generally oblong structure and comprises a liquid-permeable surface sheet 2, a liquid-impermeable back sheet 3, an absorbent part 4 disposed between the surface sheet 2 and the back sheet 3, and an intermediate portion 5, 6 disposed between the surface sheet 2 and the absorbent body 4.

The absorbent article 1 is one absorbent article elongated to the posterior in the longitudinal direction LD. Specifically, it is the absorbent article elongated to the posterior enough to cover the coccyx. The absorbent article 1 has a length of, for example 290 mm to 420 mm, preferably 330 mm to 400 mm in the longitudinal length LD. The absorbent article 1 having such an exemplified length can be suitably for lying posture when the wearer is sleeping (e.g., for nighttime use).

In use, the surface sheet 2 is positioned to the wearer's body and brought into contact with the excretion part of the body. A discharged matter such as menstrual blood discharged from the excretion part of the body passes through the surface sheet 2 and is then absorbed by the absorbent body 4. The back sheet 3 positioned toward the underwear is liquid-impermeable, so that the discharged matter cannot permeate toward the underwear but held in a state of being absorbed in the absorbent body 4.

In the present embodiment, for example, the surface sheet 2 may be a fused sheet having a two-layer structure of thermally fused fibers bound by air-through means or the like. In the two-layered fused sheet, fibers that make up structural fabrics include water-attracting and water-repelling fibers of 4 deniers or less. Specifically, the two-layered fused sheet is composed of a fabric surface layer made of a two-component composite fiber of polyethylene/polyester and a fabric back layer made of a two-component composite layer of polyethylene/polyester or polyethylene/polypropylene. In addition, the sheet member of the surface sheet 2, as well as the two-layered fused sheet, has a basis weight of 10 to 40 g/m². If the basis weight exceeds 40 g/m², the surface sheet 2 retains a liquid thereon and becomes sticky. The surface sheet 2 keeps such a sticky condition and causes the wearer discomfort. In addition, the sheet member is not limited to a specific kind as long as it has liquid permeability and a density of $0.12$ g/cm$^3$ or less. If the density of the sheet member exceeds $0.12$ g/cm$^3$, it is difficult to smoothly pass any discharged matter through the fibers of the surface sheet 2. For instance, the viscosity of menstrual blood is higher than that of urea or the like. Thus, it is preferable that the density of the sheet member is lower.

The intermediate portion 5, 6 allows the discharged matter passed through the surface sheet 2 to pass through these parts 5, 6 toward the absorbent body 4, while acting as a cushion during use. The intermediate portion 5, 6 comprises a fist intermediate sheet 5 and a second intermediate sheet 6. The details thereof will be described later.

The surface sheet 2 and the first intermediate sheet 5 can be bonded such that they are laminated together using a hot-melt adhesive and pores formed in the first intermediate layer 5. In addition, the surface sheet 2 and the second intermediate sheet 6 can be bonded such that they are laminated together using a hot-melt adhesive. In addition, the surface sheet 2, the first intermediate sheet 5, the second intermediate sheet 6, and the absorbent body 4 can be bonded such that they are laminated together using a hot-melt adhesive. Furthermore, the surface sheet 2 and the back sheet 3 are bonded such that they are laminated together by a hot-melt adhesive and a heat-sealing.

[1.2] Central Absorbent Portion and Intermediate Portion

As shown in FIG. 1, the absorbent article 1 has a generally elliptical absorbent portion 40 formed on almost the middle in the width direction WD. The absorbent portion 40 is an area surrounded by a first liquid-preventing groove 10 which will be described later. In addition, the absorbent portion 40 is an area for mainly absorbing the discharged matter from the excretion part of the body.

As shown in FIGS. 1 and 2, the absorbent portion 40 comprises at least a central absorbent portion 41 formed on the front side of the absorbent article 1 and a posterior absorbent portion 43 formed on the posterior side thereof.

The central absorbent portion 41 is formed at a location to be brought into contact with the excretion part of the body, and mainly absorbs the discharged matter from the excretion part. The central absorbent portion 41 is constructed of the surface sheet 2, the first intermediate sheet 5, and an absorbent body center portion 42, which are laminated in this order from the surface (from the body), and each of them is bonded by a hot-melt adhesive or the like such that they can be laminated together.

The posterior absorbent portion 43 absorbs, for example, the discharged matter that could not be absorbed by the central absorbent portion 41 or that comes by running along the body. The posterior absorbent portion 43 comprises the surface sheet 2, the second intermediate sheet 6, and the absorbent body posterior portion 44, which are disposed in laminate in this order from the surface (from the body). Furthermore, each of them is bonded by a hot-melt adhesive or the like to form a laminate thereof.

As shown in FIG. 2, the intermediate portion 5, 6 comprises the first intermediate sheet 5 and the second intermediate sheet 6 as described above. The first intermediate sheet 5 is disposed between the surface sheet 2 and the absorbent body center portion 42 to form a laminate thereof, while the second intermediate sheet 6 is disposed between the surface sheet 2 and the absorbent body posterior portion 44 to form a laminate thereof.

The first intermediate sheet 5 disposed on the central absorbent body portion 41 and the second intermediate sheet 6 disposed on the posterior absorbent portion 43 have different liquid-transporting properties. For instance, in the present embodiment, the first intermediate sheet 5 is superior to the second intermediate sheet 6 with respect to their liquid permeabilities. The use of the first intermediate sheet 5 of an excellent in liquid permeability allows the discharged matter from the excretion part of the body to be quickly transported to the absorbent portion 4 to prevent the wearer's sensation of wearing the sanitary napkin from becoming worse, and to prevent the discharged matter from leaking out. The liquid permeability can be represented by, for example, the permeation period of a predetermined liquid (e.g., artificial urine) in a strike-through method. The permeation period in the strike-through method can be measured using a measuring apparatus LISTER (manufactured by LENZING TECHNK). For the liquid-permeation periods of the first intermediate sheet 5 and the second intermediate sheet 6 of the present embodiment in the strike-through method, the second intermediate sheet 6 is $3.25$ seconds while the first intermediate sheet 5 is $3.07$ seconds.

In addition, for a further improvement in liquid permeability of the first intermediate sheet 5, a plurality of liquid-permeable pores 51 can be formed by carrying out a predetermined process of forming pores. Here, the pores may be formed while the first intermediate sheet 5 and the surface sheet 2 are being laminated together to allow the discharged matter from the excretion part of the body to more suitably pass through the first intermediate sheet 5 and the surface sheet 2 to reach to the absorbent portion 4. For the second intermediate sheet 6, the process of forming pores may be carried out as needed depending on a location where the second intermediate sheet 6 is disposed or depending on the specifications of a product. For instance, liquid-permeable pores 51 may be formed such that each of them has a pore size of $0.05$ mm to $3$ mm, as well as a pitch of $0.2$ mm to $10$ mm between adjacent liquid-permeable pores 51, while a pore area that occupies the second intermediate sheet is in the range of $3$ to $30\%$.

In the present embodiment, the second intermediate sheet 6 is excellent in liquid-drawing ability, compared with that of the first intermediate sheet 5. This is because, for example, the second intermediate sheet 6 on the posterior absorbent portion 43 quickly absorbs the discharged matter that could not be absorbed by the central absorbent portion 41 or that comes by running along the body to prevent the discharged matter from leaking out. The term "excellent in liquid-drawing ability" can be exemplified by any of cases having strong capillary action and an excellent hydrophilic property.

The strength of capillary action and the hydrophilic property can be represented by, for example, a liquid absorption height (g/25 mm) determined by a Klemm's absorption test described in JIS-P8141. The Klemm's absorption test was conducted on both the first intermediate sheet 5 and the second intermediate sheet 6 of the present embodiment, and the result was $25$ g/25 mm for the fist intermediate sheet 5, and $55$ g/25 mm for the second intermediate sheet 6.

Furthermore, as in the case of the present embodiment, when a sheet having an excellent liquid permeability is disposed as a first intermediate sheet 5 and a sheet having an excellent liquid-drawing ability is disposed as a second intermediate sheet 6, it is preferable that the second intermediate sheet 6 is thicker than the first intermediate sheet 5, while the second intermediate sheet 6 is longer than the first intermediate sheet 5 in the longitudinal direction LD. The second intermediate sheet 6 should be of a predetermined thickness for quickly drawing a predetermined amount of the discharged matter from the surface sheet into the absorbent body 4 for the following reasons. The second intermediate sheet 6 is disposed such that the discharged matter, such as menstrual blood flowing from the side of the central absorbent portion 41, can be prevented from leaking out of the posterior side. In addition, it is preferable to dispose the second intermediate sheet 6 as long as possible on the flow passage of the discharged matter. The first and second intermediate sheets 5, 6 may have their own thicknesses. For example, the first intermediate sheet 5 has a thickness of 0.3 mm to 0.8 mm, preferably 0.4 mm to 0.6 mm, while the second intermediate sheet 6 has a thickness of 1.0 mm to 2.0 mm, preferably 1.1 mm to 1.3 mm.

Furthermore, the first and second intermediate sheets 5, 6 may be made of different raw materials to allow these sheets 5, 6 to have different liquid-transporting properties, respectively. In addition, even if the sheets 5, 6 are prepared using the same raw material, they can be provided with different liquid-transporting properties by changing their thicknesses or densities, or subjecting them to any predetermined processing.

An example of the first intermediate sheet 5 of the present embodiment is one having a basis weight of 10 to 40 $g/m^2$ and having constitutive fibers in which a fiber system thereof is constructed of one retaining a web configuration by fusing hydrophilic fibers of 4 deniers or less at their cross-points. Specifically, it is constructed of a two-component composite fiber of polyethylene/polypropylene. The first intermediate sheet 5 has an average density of 0.03 to 0.06 $g/cm^3$, which is preferably lower than the average density of the surface sheet 2. Here, if the average density exceeds 0.06 $g/cm^3$, it becomes difficult to transport a liquid such as menstrual blood from the surface sheet 2 to the absorbent body 4, thereby increasing tendency of leaking out. Furthermore, if the average density is less than 0.03 $mg/cm^3$, the strength of absorbing the liquid such as menstrual blood from the surface of the surface sheet 2 decreases and the liquid such as menstrual blood is then retained in the surface sheet 2. Therefore, the surface sheet 2 stays sticky which causes the wearer discomfort, while liquids such as menstrual blood may run along the surface sheet 2 to the posterior side 860. Thus, such an average density is unfavorable. Furthermore, the surface sheet 2 and the first intermediate sheet 5 of the present embodiment are constructed of fibers having the same components, so that the liquid such as menstrual blood on the surface sheet 2 can be quickly transported to the absorbent body 4. The surface sheet 2 and the first intermediate sheet 5 of the present embodiment are a combination excellent in liquid permeability.

The second intermediate sheet 6 of the present embodiment can be exemplified by an airlaid nonwoven fabric having a basis weight of 60 to 200 $g/m^2$. Specifically, the airlaid nonwoven fabric is one prepared by thermal fusion of a pulp with a synthetic fiber or fixing them by a binder. The exemplified airlaid nonwoven fabric has an average density of 0.06 to 0.1 $g/cm^3$. Here, if the airlaid nonwoven fabric has an average density of 0.06 $g/cm^3$ or less, it cannot exert sufficient drawing property and diffusion properties. Furthermore, if the average density of the airlaid nonwoven fabric exceeds 0.1 $g/cm^3$, a liquid such as menstrual blood cannot be quickly transported to the absorbent body 4. Thus, the liquid such as menstrual blood is retained in the second intermediate sheet 6. Therefore, it may result in sticky condition which discomforts the wearer, so that an excessive average density of the airlaid nonwoven fabric is unfavorable.

The absorbent article 1 of the present embodiment comprises a first intermediate sheet 5 disposed between the surface sheet 2 and the absorbent body center portion 42 on the central absorbent portion 41. Here, the first intermediate sheet 5 has an excellent liquid permeability and transports a large amount of the discharged matter such as menstrual blood to the absorbent part. In addition, the absorbent article 1 also comprises the second intermediate sheet 6 disposed between the surface sheet 2 and the absorbent body posterior portion 44 on the posterior absorbent portion 43. Here, the second intermediate sheet 6 quickly absorbs and draws a small amount of the discharged matter such as menstrual blood from the side of the surface sheet 2. The absorbent article 1 of the present embodiment comprises intermediate layers 5, 6 disposed on different locations on the absorbent article 1. In other words, the intermediate layers 5, 6 have different transporting properties depending on the parts of the body to be brought into contact therewith.

Furthermore, in the present embodiment, parts of the first and second intermediate sheets 5 and 6 are disposed in laminate on the central absorbent portion 41. Therefore, the absorbent article is provided with an improved absorbability on the central absorbent portion 41, as well as an increased thickness enough to improve its strength and shape-retaining property, thereby preventing the absorbent portion 40 from twisting when it absorbs the liquid such as menstrual blood. Consequently, the absorbent article can inhibit the generation of a gap between the absorbent portion 40 and the body, thereby preventing the discharged matter such as menstrual blood from leaking out.

[1.3] Mode of Usage

Referring now to FIGS. 3 and 4, an exemplified mode of usage of the absorbent article according to the present invention will be described with reference to the absorbent article according to the first embodiment of the present invention.

As an example of the mode of usage of the absorbent article 1 when the wearer takes a lying posture while sleeping. As shown in FIG. 3, in the state of using in lying posture, the posterior side 860 of the absorbent article 1 is disposed to extend substantially parallel to the floor, while the front side 840 thereof is disposed to form a predetermined angle with the posterior side 860 of the absorbent article 1, or the front side 840 is disposed to form a predetermined angle with the floor. In common with the conventional absorbent article, the wearer folds back the wing flaps W1, W2 and fixes them on underwear or the like through adhesive parts 7, 8.

Here, each of the wing flaps w1, w2 are formed such that a part of the surface sheet 2 extends laterally, while the part of the back sheet 3 extends outwardly in the width direction WD, and the extended portion of the surface sheet 2 and the extended portion of the back sheet 3 are bonded by a hot-melt adhesive.

The central absorbent portion 41 is brought into contact with the excretion part of the wearer's body by means of external forces, such as tension of the underwear and pressing forces of the thighs. However, when the wearer is in a lying posture while sleeping or the like, the excretion part of the body, such as the vaginal opening, faces substantially perpendicular to the floor. Thus, the discharged matter such as menstrual blood tends to flow to the floor by gravitation. In other words, the discharged matter from the excretion part of the body is absorbed by the central absorbent portion 41 on the front side 840 which is substantially disposed to the floor, but in some situations the discharged matter may flow along the body to the posterior side 860 because of being left in the state as shown in FIG. 3 for prolonged period of time. For instance, when the amount of the discharged matter exceeds the absorption amount of the central absorbent portion 41 or when a gap between the body and the absorbent article 1 is formed by movements of the wearer, such as rolling over during sleep, the discharged matter such as menstrual blood along the posterior groove of the wearer or the like, thereby facilitating the back leakage or diagonally back leakage of the discharged matter such as menstrual blood.

As shown in FIG. 4, while the absorbent article 1 is being attached to the underwear or the like, the central absorbent portion 41 is in a state of being inclined at a predetermined angle with respect to the posterior side 860 disposed on the floor side. The central absorbent portion 41 is brought into contact with the excretion part of the body facing substantially perpendicular to the floor and then absorbs the discharged matter.

In the case of using the absorbent article 1 while sleeping or the like, when the discharged matter is discharged more than the limit absorption amount of the absorbent body center portion 42 on the central absorbent portion 41, the central absorbent portion 41 becomes sticky and causes the wearer discomfort. Furthermore, because of exceeding the absorption amount limit of the absorbent body center portion 42, the unabsorbed portion of the discharged matter may flow to the posterior side 860 of the absorbent article 1.

Here, for preventing the feeling of wearing from declining or preventing the discharged matter from leakage (back-leakage) from the posterior side 860, the first intermediate sheet having an excellent liquid permeability is disposed on the central absorbent portion 41 to quickly transport the discharged matter from the surface sheet 2 to the absorbent body 4. For instance, the first intermediate sheet 5 employed in the present embodiment is able to transport the discharged matter to the absorbent body 4 without causing accumulation of the discharged matter in the first intermediate sheet 5. In addition, the first intermediate sheet 5 is disposed just under the location on the surface sheet 2 to be brought into direct contact with the excretion part of the body. Besides, a large amount of the discharged matter is discharged from the excretion part of the body, so that the discharged matter can be quickly transported to the absorbent body 4 by the self-weight of the discharged matter.

Furthermore, for absorbing the discharged matter flown to the posterior side 860 before it leaks from the posterior of the posterior side 860, the second intermediate sheet 6 having a high hydrophilic property can be disposed. In the present embodiment, for example, a second intermediate sheet 6 having a strong capillary action and a high degree of hydrophilicity can be disposed. Thus, the second intermediate sheet 6 draws the discharged matter such as menstrual blood from the surface sheet 2 to prevent the discharged matter from flowing along the surface sheet 2. The discharged matter such as menstrual blood flowing from the central absorbent portion 41 is mainly a liquid but small in amount, so that it is difficult to be transported to the absorbent body 4 because of its poor weight. In addition, the central absorbent portion 41 is in a state of being raised at a predetermined angle with respect to the posterior absorbent portion 43, so that the discharged matter can be flown at a predetermined rate. Therefore, it is preferable to dispose the second intermediate sheet 6 having a high liquid-drawing ability to prevent the discharged matter from back-leakage.

The absorbent article 1 is provided with a folding part 850 formed substantially perpendicular to the longitudinal direction LD of the absorbent article 1. The folding part 850 allows the absorbent article 1 to be folded. In the present embodiment, the first intermediate sheet 5 is disposed only on the front side with respect to the folding part. In other words, the first intermediate sheet 5 is not disposed on the posterior side with respect to the folding part 850.

The second intermediate sheet 6 extends from the front side to the posterior side with respect to the folding part 850 and thus it is disposed over the folding part 850. The front side of the second intermediate sheet 6 with respect to the folding part 850 is disposed in laminate under the surface sheet 2 and the first intermediate sheet 5 (on the side of the absorbent body 4). On the other hand, the posterior side of the second intermediate sheet 6 is disposed in laminate under the surface sheet 2 (on the side of the absorbent body 4).

Here, by disposing the first and second intermediate sheet 5, 6 on the absorbent article 1, for example, the central absorbent portion 41 of the absorbent article 1 can be imparted with strength and shape-retaining property. Thus, it prevents the central absorbent portion 41 from twisting when the discharged matter is absorbed, so that it will contribute to fit the absorbent article 1 to the part of the body extending from the perineal area to the coccyx, where the conventional absorbent article is difficult to fit.

[1.4] Production

The absorbent article 1 can be produced by, for example, a manufacturing process containing the following procedures. For instance, a first intermediate sheet 5 is disposed on a surface sheet 2 and then laminated and bonded together by a hot-melt adhesive or the like. Subsequently, the surface sheet 2 and the first intermediate sheet 5 are subjected to the process for forming pores to form them in the whole or a part of their laminated areas.

After carrying out the process for forming pores, the second intermediate sheet 6 is disposed such that part thereof is laminated on the first intermediate sheet 5 and the remaining part thereof is laminated only on the surface sheet 2, and then laminated together by a hot-melt adhesive or the like. Subsequently, the back sheet 3 is disposed to cover the first and second intermediate sheets 5, 6 and then laminated together by a hot-melt adhesive and heat-sealing, thereby resulting in a combined structure.

[2] Second Embodiment

As shown in FIGS. 5 and 6, an absorbent article 1A according to a second embodiment of the present invention is configured by the same way as that of the first embodiment, excepting that a first intermediate sheet 5 is disposed in parallel to a second intermediate sheet 6 in the thickness direction without overlapping each other.

Here, just as in the case of the absorbent article 1 of the first embodiment, a first intermediate sheet 5 is disposed in lamination between a surface sheet 2 and an absorbent body center portion 42. In addition, the first intermediate sheet 5 is disposed only on the front side 840 of the absorbent article 1 with respect to a folding part 540 (see FIG. 3).

The second intermediate sheet 6 is disposed in laminate between the surface sheet 2 and the absorbent body posterior portion 44. In addition, the second intermediate sheet 6 is disposed on the posterior side 860 of the absorbent article 1. Furthermore, the second intermediate sheet 6 is mainly disposed on the posterior side with respect to the folding part 540. Besides, the second intermediate sheet 6 is disposed such that it continuously extends along the first intermediate sheet 5 in a planar manner.

Such an arrangement allows an absorbent portion 40 to be thinner than that of the absorbent article 1 of the first embodiment. Thus, the arrangements of the first and second intermediate sheets 5, 6 can be properly controlled depending on the specifications of a product. Here, the arrangements, configurations, and so on of the first and second intermediate sheets 5, 6 are not limited to the aspects shown in the first and second embodiments.

[3] Each of Structural Components

Hereinafter, each of structural components will be described in detail.

The surface sheet 2 is formed in the shape of a resin film having a plurality of liquid-passage pores, a net sheet having a plurality of mesh pores, nonwoven fabric having liquid permeability, fabric, or the like. The resin film or net sheet used may be any of those prepared from polypropylene (PP), polyethylene (PE), polyethylene terephthalate (PET), and so on. In addition, nonwoven fabric used for the surface sheet 2 may be any of spunlaced nonwoven fabrics made of cellulose fibers such as rayon and synthetic resin fibers and air-through nonwoven fabrics made of the synthetic resin fibers. In addition, the raw material of the nonwoven fabric used for the surface sheet 2 may be any of biodegradable natural products, such as polylactic acid, chitosan, and polyalginic acid. As an alternative example, furthermore, the surface sheet 2 may be formed with a plurality of liquid-passage pores in the surface thereof, while a silicon- or fluorine-based water-repellent oil solution is applied thereon to provide a sheet having an external surface on which the body fluid can be hardly attached.

Furthermore, not only confining to the above nonwoven fabric, the basis weight of a sheet member that constitutes the surface sheet 2 is preferably 15 to 100 $g/m^2$, more preferably 20 to 50 $g/m^2$, particularly preferable 10 to 40 $g/m^2$. If the basis weight is less than 15 $g/m^2$, a sufficient surface strength cannot be obtained. Thus, it could lead to be broken in use. If the basis weight exceeds 100 $g/m^2$, extreme roughness can be generated to make the wearer uncomfortable in use. In the case of using the absorbent article 1 for a prolonged time period, when the basis weight exceeds 40 $g/m^2$, the surface sheet 2 retains a liquid thereon and becomes sticky. The surface sheet 2 keeps such a sticky condition and makes the wearer discomfort. Furthermore, the sheet member that constitutes the surface sheet 2 is not subjected to suction absorption to make pores as far as it has a density of 0.12 $g/cm^3$ or less, while having liquid permeability. If the density of the sheet member that constitutes the surface sheet 2 is higher than 0.12 $g/cm^3$, a liquid can be difficult to pass smoothly through the space between the fibers of the sheet member that constitutes the sheet part 2. In the case of menstrual blood, because of its higher viscosity compared with urea or the like, it is preferable that the density of the sheet member of the surface sheet 2 is sufficiently lower than 0.12 $g/cm^3$.

Furthermore, when the surface sheet 2 is a pore film such as one having a plurality of the above liquid-passage pores 51, it is preferable that the pore sizes are in the range of 0.05 mm to 3 mm and the pitches of the pores 51 are in the range of 0.2 mm to 10 mm, and the pore area that occupies the surface sheet 2 is in the range of 3% to 30%. A process for producing such a surface sheet 2 may be, for example, the so-called PFW method in which a film is fed through a pattern drum under previously varied conditions of opening pores and then subjected to suction absorption to make pores, or may be a process using pin-embossment for further providing the area over the folding line of the surface sheet 2 obtained by a PFW method having uniform conditions for opening pores. The pores may be aligned in a zigzag-, lattice-, or wave-like pattern or the like, but not specifically limited. In addition, the shapes of the pores include round, oval, and square shapes. In addition, the pore may have a valve on its peripheral edge. Preferably, nonwoven fabrics with or without pores or porous plastic sheets may be used.

Furthermore, as a preferred example of the surface sheet 2 as described above, a two-layered fusion sheet having thermal fusion fibers bonded together by air-through means or the like can be used. In the two-layered fusion sheet, a fiber system of constitutive fibers is constructed of hydrophilic fibers and water-repellent fibers of 4 deniers or less. Specifically, the two-layered fusion sheet comprises a fabric surface layer made of a two-component composite fiber of polyethylene/polyester and a fabric back layer made of a two-component composite layer of polyethylene/polyester or polyethylene/polypropylene. In addition, the sheet member of the surface sheet 2, as well as the two-layered fusion sheet, has a basis weight of 10 to 40 $g/m^2$. If the basis weight exceeds 40 $g/m^2$, the absorbent article 1 is compelled to retain a liquid in the surface sheet 2. As a result, the absorbent article 1 is being sticky for the wearer and makes the wearer discomfort.

A back sheet 3 may be a material capable of preventing a discharged matter absorbed in an absorbent body 4 from leaking out. In addition, the back sheet 3 may be made of a moisture-permeable raw material to make possible to decrease steamy conditions in wear, thereby improving the feeling of discomfort in wear. The materials for the back sheet 3 include a liquid-impermeable film mainly comprising polyethylene (PE), polypropylene (PP), or the like, an air-permeable film, and a composite sheet prepared by laminating a liquid-impermeable film on one side of a spun-bonded nonwoven fabric or the like. Preferably, a laminate of a hydrophilic nonwoven fabric or an impermeable plastic film with an impermeable plastic film can be used. Alternatively, it may be a SMS nonwoven fabric sandwiched by melt-blown nonwoven fabrics having high water-resisting property and high-strength spun-bonded nonwoven fabrics.

The first and second intermediate sheets 5, 6 are liquid-permeable sheets disposed between the surface sheet 2 and the absorbent body 4. Each of the first and second intermediate sheets 5, 6 can be prepared using a material, such as a resin film on which a plurality of liquid-passage pores is formed along with the surface sheet 2, a net sheet having a plurality of mesh pores, a liquid-permeable nonwoven fabric, or a fabric. The resin film or net sheet used is one made of polypropylene (PP), polyethylene (PE), polyethylene terephthalate (PET), or the like. In addition, the nonwoven fabric used may be any of spunlaced nonwoven fabrics made of cellulose fibers such as rayon and synthetic resin fibers and air-through nonwoven fabrics made of the synthetic resin fibers. Furthermore, the first and second intermediate sheets 5, 6 play their roles in supporting the absorbent part 5 to provide the absorbent body 4 with flexibility and stability in shape.

Furthermore, as described above, a preferable example of the sheet member that constitutes the first intermediate sheet 5 is one having a basis weight of 10 to 40 $g/m^2$ and having constitutive fibers in which a fiber system thereof is constructed of one retaining a web configuration by fusing hydrophilic fibers of 4 deniers or less at their cross-points. Specifically, it is constructed of a two component composite fiber of polyethylene/polypropylene. The sheet member that constitutes the first intermediate sheet 5 has an average density of 0.03 to 0.06 $g/cm^3$, which is preferably lower than the average density of the surface sheet 2. Here, if the average density exceeds 0.06 $g/cm^3$, it becomes difficult to transport a liquid such as menstrual blood from the surface sheet 2 to the absorbent body 4, thereby increasing tendency of leaking out. Furthermore, if the average density is less than 0.03 $mg/cm^3$, the strength of absorbing the liquid such as menstrual blood from the surface of the surface sheet 2 decreases and the liquid such as menstrual blood is then retained in the surface sheet 2. Therefore, the absorbent article 1 becomes sticky and makes the wearer discomfort, while the liquid such as menstrual blood may run along the surface sheet 2 to the posterior side 860. Thus, such an average density is unfavorable.

Furthermore, likewise, an example of the sheet member that constitutes the second intermediate sheet 6 of the present embodiment can be an airlaid nonwoven fabric having a basis weight of 60 to 200 g/m². Specifically, the airlaid nonwoven fabric is one prepared by thermal fusion of a pulp with a synthetic fiber or fixing them by a binder. The airlaid nonwoven fabric may have an average density of 0.06 to 0.1 g/cm³. Here, if the airlaid nonwoven fabric has an average density of 0.06 g/cm³ or less, it cannot exert sufficient drawing property and diffusion properties. Furthermore, if the average density of the airlaid nonwoven fabric exceeds 0.1 g/cm³, a liquid such as menstrual blood cannot be quickly transported to the absorbent body 4. Thus, the second intermediate sheet 6 retains the liquid such as menstrual blood, so that it may result in sticky condition and make the wearer discomfort. Therefore, an excessive average density of the airlaid nonwoven fabric is unfavorable.

The intermediate portions 5, 6 are laminated together with the surface sheet 2 by a predetermined hot-melt adhesive. For instance, the hot-melt adhesive is applied such that a plurality of thin lines extending in the longitudinal direction LD on the center portion of the intermediate portions 5, 6 in the width direction WD. Therefore, the intermediate portions 5, 6 are bonded together.

As described above, it is desirable that the intermediate sheet 5, 6 comprises a first intermediate sheet 5 and a second intermediate sheet 6. The width dimension A1 of the first intermediate sheet 5 (see FIG. 1) is preferably 30 to 80 mm, more preferably 50 to 70 mm in the absorbent article 1 of the first embodiment. If the width dimension A1 is less than 30 mm, the width to continuously contact with the vaginal opening is insufficient, so that the gap between the wearer's body and the sanitary napkin may be formed, thereby increasing a tendency of leaking out. In contrast, when the width dimension A1 exceeds 80 mm, it is not preferable because of extending over the crotch's width of underwear such as shorts.

It is desirable that the length dimension A2 of the first intermediate sheet (see FIG. 1) is, for example, 50 to 120 mm, preferably 60 to 100 mm. For instance, the front end of the first intermediate sheet 5 is located at 30 mm or more, preferably 50 mm or more anterior with respect to the locations of the center portions WP of the respective wing flaps W1, W2 in the longitudinal direction LD. In addition, the posterior end of the first intermediate sheet 5 is located at 20 to 70 mm, preferably 30 to 50 mm posterior with respect to the location of the center portions WP of the respective wing flaps W1, W2 in the longitudinal direction LD. If the posterior end is located at more than 70 mm posterior to the center portions WP of the wing flaps W1, W2, menstrual blood or the like flows along the surface sheet 2, thereby facilitating the back-leakage thereof.

It is desirable that the width dimension B1 of the second intermediate sheet 6 is, for example for the absorbent article 1 of the first embodiment, 10 to 40 mm, preferably 15 to 30 mm. If the width dimension B1 is less than 10 mm, the width to keep contact with the posterior groove from the perineal area to the coccyx may be insufficient. In addition, the gap between the wearer's body and the absorbent article 1 tends to be generated, so that the discharged matter may be facilitated to leak out. In contrast, when the width dimension B1 exceeds 40 mm, it is not preferable because of extending over the crotch's width of underwear such as shorts. It becomes difficult to fit the absorbent article to the posterior groove.

It is desirable that the width dimension B2 of the second intermediate sheet 6 is, for example for the absorbent article 1A of the second embodiment, 50 to 130 mm, preferably 60 to 110 mm. In the second embodiment, it is preferable that the front end of the second intermediate sheet 6 is located at the posterior end of the first intermediate sheet 5. Then, it is desirable that the posterior end is located within 150 mm or less, more preferably within 120 mm or less with respect to the location of the center portions WP of the respective wing flaps W1, W2 in the longitudinal direction LD. IF the posterior end is more than 150 mm far from the center portions WP of the respective wing flaps W1, W2, the second intermediate sheet 6 is disposed such that it extends posterior to the coccyx. Thus, the wearer feels the amount of the second intermediate sheet 6, so that he wearer may feel uncomfortable during wear.

The liquid permeability can be represented, for example, by the permeation period of a given liquid measured by a strike-through method. Specifically, it can be measured as follows: In a cylindrical vessel of about 10 mm in diameter equipped with electrodes, 10 ml of artificial urea (composition: a mixture of (1) urea (first grade chemicals) (200 g), (2) sodium chloride (Japanese Pharmacopoeia, exclusive use in production) (80 g), (3) magnesium sulfate (heptahydrate) (first grade chemicals) (8 g), (4) calcium chloride (dihydrate) (first grade chemicals) (3 g), and (5) blue dye No. 1 (about 1 g)) and then a measuring object is placed. Subsequently, a time required for running the liquid out of the cylindrical vessel after initiating the flow of a liquid to the measuring object is measured as a permeation period. Specifically, the flow of electricity occurs through the liquid but it does not occur in the absence of the liquid, so that the conducting time is measured as a permeation period of the measuring object. Here, for example, the permeation period in the strike-through method can be measured using a measuring device LISTER (manufactured by LENZING TECKHNK, Co., Ltd.).

The liquid-drawing ability can be confirmed and represented by the strength of capillary action, the degree of hydrophilicity, or the like. In particular, the strength of capillary action or the degree of hydrophilicity can be determined as follows: In the Klemm's absorption test as described in JIS-P8141, the measuring object is immersed in the above artificial urea for 5 minutes and then the absorption height of the artificial urea (g/25 mm) is measured. The strength of capillary action or the degree of hydrophilicity can be represented by the measured absorption height (g/25 mm).

The absorbent body 4 is constructed of an absorbent material and a cushion disposed on the side of the surface sheet 2. The absorbent material is preferably a bulky material having functions of absorbing and retaining a liquid such as menstrual blood and also having a mild chemical stimulus, while hardly losing its shape. An example of such an absorbent material is constructed of a fluff pulp or an airlaid nonwoven fabric as well as a high-absorbance polymer. Examples of the fluff pulp include chemical pulps, cellulose fibers, and artificial cellulose fibers such as rayon and acetate. Examples of the airlaid nonwoven fabric include a nonwoven fabric prepared by subjecting a pulp and a synthetic fiber to thermal fusion or fixing them by a binder. Examples of the high-absorbance polymer include starch-, acrylic acid-, and amino acid-based granular or fibrous polymers. In addition, examples of the nonwoven fabrics include spun-laced, spun-bonded, thermal-bonded, melt-blown, needle-punched, and air-through nonwoven fabrics. Raw material fibers which can constitute the nonwoven fabrics include olefin (such as polyethylene or polypropylene)-, polyester-, and polyamide-based synthetic fibers, as well as regenerated fibers such as rayon and cupra, and natural fibers such as cotton. Examples of the cushion include liquid-permeable paper and a cellulose sheet part. As an example of the absorbent body 4 prepared by a combination of the cushion and the absorbent material, one containing a pulp having a basis weight of 200 g/m² and a polymer having a basis weight of 4 g/m² (the polymer is dispersed entirely), where a mixture of the pulp and the polymer which are uniformly dispersed all over is wrapped in tissue of 15 g/m² in basis weight.

The shape of configuration of the absorbent body 4 may be changed if required. The total absorption amount of the absorbent part 5 should be corresponded to the design insertion amount and desired usage of the absorbent article. In addition, the dimensions, absorbing ability, and so on of the absorbent body 4 vary so as to correspond to each of child and adult wearers.

A first liquid-preventing groove 10 comprises a front-side U-shaped portion formed in a generally U-shape and extended to the front side in the longitudinal direction LD, inner lateral portions continuously extended from the opposite sides of the front-side U-shaped portion in the longitudinal direction LD, respectively, a posterior-side U-shaped portion formed in a generally U-shape connecting the posterior-side ends of the inner lateral portions and extended to the posterior side in the longitudinal direction LD.

The first liquid-preventing groove 10 is, as a whole, a longitudinally extended, generally elliptical shape and formed so as to surround the absorbent portion 40.

A second liquid-preventing groove 11 comprises outer lateral portions formed and substantially, equally spaced so as to be extend along the outsides of the inner lateral portions of the first-preventing groove 10 in the longitudinal direction LD, and an outside U-shaped portion formed in a generally U-shape connecting the posterior-side ends of the outer lateral portions and extended to the posterior side in the longitudinal direction LD.

The first and second liquid-preventing grooves 10, 11 are formed by a pressure-bonding part 9 which is continuously formed by a predetermined press-bonding process. The pressure-bonding part 9 may be formed by a predetermined press-bonding process using a heating roller. For instance, when the first and second liquid-preventing grooves 10, 11 are formed, a roller having a flat surface is brought into contact with the back sheet 3 of the absorbent body 4, and also a heating roller having predetermined protrusion patterns is brought into contact with the surface of the surface part 2, followed by pressing and heating them, respectively. Consequently, on the pressure bonding part 9, a plurality of medium-density pressure-bonding parts having densities higher than those of areas other than the pressure-bonding part 9, but not formed in a film shape, is formed between a plurality of high-density pressure-bonding parts, where the absorbent body 4 and the surface sheet 2 are substantially formed into films by pressure-bonding, and a high-density pressure-bonding part adjacent to the high-density pressure-bonding parts. In all portions of the patterns of the pressure-bonding part 9, the high-density pressure-bonding parts and the medium-density pressure-bonding parts are formed one after the other, thereby forming first and second liquid-preventing grooves 10, 11 that extend linearly and hollow from the surface of the absorbent article 1 (from the body side) to the side of the back sheet 3.

It is desirable that, for example for the absorbent article 1 of the first embodiment, the first and second liquid-preventing grooves 10, 11 may have width dimensions of 0.5 to 10 mm, preferably 1 to 5 mm. If the width dimension is less than 0.5 mm, the grooves are only provided for separating the surface sheet 2 from the absorbent body 4. If the width dimension exceeds 10 mm, the grooves produce a reduction in fitness, sense of use, absorbability, or the like.

Furthermore, it is desirable that the disposed distance C1 between the first and second liquid-preventing grooves 10, 11 is 1 to 10 mm, preferably 5 to 8 mm. If the distance is less than 1 mm, a reduction in fitness, sense of use, or the like may occur. If the distance C1 exceeds 10 mm, a reduction in fitness, as well as twisting of the absorbing portion 10, tends to occur.

Furthermore, it is desirable that the spaced distance between the both sides of the first liquid-preventing groove 10, which is in a direction perpendicular to the centerline CL, is 20 to 60 mm, preferably 30 to 40 mm. If the distance is less than 20 mm, the absorbent portion 40 hardly keeps its contact with the external part of the wearer's body (vaginal opening) and a gap between the wearer's body and the absorbent article 1 may be formed, thereby increasing a tendency of leaking out. If the distance exceeds 60 mm, the center of the absorbent portion 40 is deformed in a concaved shape. Thus, a gap between the wearer's body and the absorbent article 1 may be formed, thereby increasing a tendency of leaking out.

Adhesives for adhesive parts 7, 8 may be any of adhesive compounds such as an acrylic pressure sensitive adhesive and a rubber pressure sensitive adhesive, cellulose- and polyvinyl alcohol-based adhesives, gelatin, and polyamino acid gels such as polyglutamic acid and polylysine, which exert adhesion forces by firmly attaching to the skin.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article, comprising:
a liquid-permeable surface sheet;
a liquid-impermeable back sheet; and
an absorbent body disposed between the surface sheet and the back sheet, wherein the absorbent body comprises:
an absorbent body center portion, and
an absorbent body posterior portion continuously formed on a posterior side, in a longitudinal direction of an absorbent body center portion; and
an intermediate sheet portion being disposed between the surface sheet and the absorbent body, wherein the intermediate sheet portion comprises:
a first intermediate sheet is disposed between the surface sheet and the absorbent body center portion, and
a second intermediate sheet disposed between the surface sheet and at least the absorbent body posterior portion, a liquid-transport property of the second intermediate sheet being different from a liquid-transport property of the first intermediate sheet; and
a folding part, predetermined to be folded substantially perpendicular to the longitudinal direction,
wherein the first intermediate sheet is disposed only on one side of the folding part in the longitudinal direction.

2. The absorbent article according to claim 1, wherein the liquid-transport property is liquid permeability, and the first intermediate sheet has a higher liquid permeability than the second intermediate sheet.

3. The absorbent article according to claim 2, wherein the first intermediate sheet is further provided with a plurality of liquid-permeable pores.

4. An absorbent article according to claim 3, wherein a part of the second intermediate sheet is disposed in laminate, being overlapped in a direction of width by at least a part of the first intermediate sheet.

5. The absorbent article according to claim 4,
wherein the second intermediate sheet is disposed over the folding part and extends from one side to another side of the folding part.

6. The absorbent article according to claim 5, wherein the second intermediate sheet is thicker than the first intermediate sheet, and the second intermediate sheet is longer than the first intermediate sheet in the longitudinal direction.

7. The absorbent article according to claim 1, wherein the liquid-transport property is a liquid-drawing ability, and the second intermediate sheet has a higher liquid-drawing ability than the first intermediate sheet.

8. The absorbent article according to claim 7, wherein the second intermediate sheet has a stronger capillary action than the first intermediate sheet.

9. An absorbent article according to claim 8, wherein a part of the second intermediate sheet is disposed in laminate, being overlapped in a direction of width by at least a part of the first intermediate sheet.

10. The absorbent article according to claim 7, wherein the second intermediate sheet has a higher hydrophilic property than the first intermediate sheet.

11. An absorbent article according to claim 10, wherein a part of the second intermediate sheet is disposed in laminate, being overlapped in the direction of width by at least a part of the first intermediate sheet.

12. The absorbent article according to claim 1, wherein the second intermediate sheet is continuously disposed parallel with the first intermediate sheet in the longitudinal direction.

13. The absorbent article according to claim 1,
wherein the second intermediate sheet is disposed over the folding part and extends from one side to another side of the folding part.

14. The absorbent article according to claim 13, wherein the second intermediate sheet is thicker than the first intermediate sheet, and the second intermediate sheet is longer than the first intermediate sheet in the longitudinal direction.

15. An absorbent article, comprising:
a liquid-permeable surface sheet;
a liquid-impermeable back sheet; and
an absorbent body disposed between the surface sheet and the back sheet, wherein the absorbent body comprises:
an absorbent body center portion, and
an absorbent body posterior portion continuously formed on a posterior side, in a longitudinal direction of an absorbent body center portion; and
an intermediate sheet portion being disposed between the surface sheet and the absorbent body, wherein the intermediate sheet portion comprises:
a first intermediate sheet disposed between the surface sheet and the absorbent body center portion, and
a second intermediate sheet disposed between the surface sheet and at least the absorbent body posterior portion, a liquid-transport property of the second intermediate sheet being different from a liquid-transport property of the first intermediate sheet; and
a folding part, predetermined to be folded substantially perpendicular to the longitudinal direction,
wherein the first intermediate sheet is disposed one on one side of the folding part in the longitudinal direction, and the second intermediate sheet is disposed over the folding part and extends from the one side to another side of the folding part.

* * * * *

UNITED STATES PATENT AND TRADEMARK OFFICE
CERTIFICATE OF CORRECTION

PATENT NO. : 7,727,213 B2  Page 1 of 1
APPLICATION NO. : 11/540029
DATED : June 1, 2010
INVENTOR(S) : Takashi Nomoto and Chinatsu Nanbu It is certified that error appears in the above-identified patent and that said Letters Patent is hereby corrected as shown below:

In the Abstract

In column 2, line 11, under "ABSTRACT", delete "D" and substitute --LD-- in its place.

In the Specification

In column 7, line 12, delete the last word "fist" and substitute --first-- in its place.

Signed and Sealed this

Ninth Day of November, 2010

David J. Kappos
*Director of the United States Patent and Trademark Office*